United States Patent [19]

Suzuki

[11] Patent Number: 4,565,545
[45] Date of Patent: Jan. 21, 1986

[54] CATHETER INSERTION DEVICE
[75] Inventor: Tatsuo Suzuki, Yokohama, Japan
[73] Assignee: Terumo Kabushiki Kaisha, Tokyo, Japan
[21] Appl. No.: 726,185
[22] Filed: Apr. 23, 1985

Related U.S. Application Data

[63] Continuation of Ser. No. 422,397, Sep. 24, 1982, abandoned.

[30] Foreign Application Priority Data

Jun. 4, 1982 [JP] Japan ......................... 57-82293[U]

[51] Int. Cl.⁴ ............................................. A61M 5/00
[52] U.S. Cl. ..................................... 604/164; 604/272
[58] Field of Search ............... 604/117, 239, 272–274, 604/164–169

[56] References Cited

U.S. PATENT DOCUMENTS

| | | | |
|---|---|---|---|
| 2,830,587 | 4/1958 | Everett | 604/272 |
| 3,094,122 | 6/1963 | Gauthier et al. | 604/164 |
| 3,308,822 | 3/1967 | DeLuca | 604/274 |
| 3,633,580 | 1/1972 | Knox | 604/274 |
| 3,788,320 | 1/1974 | Dye | 604/165 |
| 4,335,718 | 6/1982 | Calabrese | 604/272 |

FOREIGN PATENT DOCUMENTS

| | | | |
|---|---|---|---|
| 711902 | 10/1941 | Fed. Rep. of Germany | 604/272 |
| 2481931 | 11/1981 | France | 604/168 |

Primary Examiner—Dalton L. Truluck
Attorney, Agent, or Firm—Frishauf, Holtz, Goodman & Woodward

[57] ABSTRACT

Since a typical catheter insertion device is used for percutaneous insertion of a catheter into an artery or a vein located in a deep part of a tissue, it is necessary to secure a sufficient lumen for introducing the catheter while alleviating pain inflicted on the patient when the catheter insertion device punctures the artery or the vein. The catheter insertion device of the invention has a tapered portion formed in the vicinity of a beveled surface of an inner needle in order to realize both necessary functions. Accordingly, it is possible to decrease the size of the incision in the tissue because it is formed by the beveled surface of the tapered needle point with a smaller diameter, and the desired objects can be accomplished by means of an elastic insertion of the catheter into the smaller incision and, at the same time, bleeding from the incision can be minimized.

9 Claims, 16 Drawing Figures

CATHETER INSERTION DEVICE

This application is a continuation of application Ser. No. 422,397, filed Sept. 24, 1982, now abandoned.

BACKGROUND OF THE INVENTION

1. Field of the Invention

The present invention relates to a catheter insertion device capable of securing a passage communicating with a blood vessel in such a manner that a device comprising an outer catheter and an inner needle received thereby is thrust into a blood vessel, and when the outer catheter has entered into the blood vessel, the inner needle is pulled out to secure a passage communicating with a blood vessel by means of the outer catheter.

2. Description of the Prior Art

The catheter insertion device has been widely used for securing a lumen for introducing a catheter by thrusting the catheter insertion device into a blood vessel located in a relatively deep part of the body tissue of a patient. A conventional catheter insertion device with a typical arrangement will be described hereinunder, with reference to the accompanying drawings for easier understanding.

The catheter insertion device, shown in FIG. 1, comprising an inner needle 1 and an outer catheter 2 fitted on the outside of the inner needle 1, inevitably makes an incision 4 with a size (a) equal to the beveled surface width of the inner needle 1, i.e., the diameter of the inner needle 1 when the catheter insertion device is thrust into a blood vessel 3 as shown in FIG. 2. Therefore, hemostasis after the needle is pulled out becomes more difficult with the increase in the outside diameter of the inner needle 1. On the other hand, when the catheter insertion device is used as a needle for introducing an angiography catheter, the inner catheter is pulled out with a guide wire being indwelled in the blood vessel. In other words, after the catheter insertion device is thrust into the blood vessel, the inner needle is pulled out with the outer catheter left and subsequently the guide wire is introduced into the blood vessel by using the outer catheter as an introducing needle. Under this condition, a large amount of blood flows out from the incision to the outside until an angiography catheter, not shown, is introduced into the blood vessel with the guide wire used as a guide, because the guide wire used has an outside diameter equal to or smaller than the width (a) of the incision 4.

The above-mentioned problems have been solved by means of a catheter insertion device shown in FIG. 3. The catheter insertion device is provided with a dilator 5 disposed between the inner needle 1 and the outer catheter 2 and having on its end outer surface a dilator tapered tip portion 5a capable of enlarging the incision 4 in the blood vessel formed by means of the beveled point of the inner needle 1. Accordingly, although the width (a) of the incision 4 in the blood vessel 3 shown in FIG. 2 is equal to the diameter of the inner needle 1 even if the catheter insertion device of this type is used, the incision becomes smaller and hemostasis becomes easier because the diameter of the inner needle 1 is smaller than the inside diameter of the outer catheter 2 (e.g., the inside diameter of the outer catheter 2 is 1 mm while the outside diameter of the inner needle 1 is 0.8 mm). Moreover, when the catheter insertion device is used as a needle for introducing the angiography catheter, the guide wire is clamped by the blood vessel wall when the guide wire is being indwelled in the blood vessel, because the guide wire diameter (e.g., 1 mm $\phi$) is larger than the blood vessel incision (e.g., 0.8 mm) shown in FIG. 2. Therefore, only a small amount of blood leaks from the incision 4 (however, the relationship between the ratio of the blood vessel incision to the guide wire diameter and the amount of leakage blood has not been accurately known).

However, the production cost of the catheter insertion device of this kind is considerably higher than that of the catheter insertion device shown in FIG. 1 because the former has the dilator 5. Moreover, because the penetration resistance of the tip of the dilator tapered tip portion 5a is added to the penetration resistance of the catheter insertion device shown in FIG. 1, the patient suffers a correspondingly larger pain. Furthermore, because there is the dilator 5 and consequently the length $l_1$ between the beveled point of the inner needle 1 and the outer catheter tapered portion is larger than that of the catheter insertion device shown in FIG. 1, it is frequent that the end of the outer catheter 2 does not enter into the blood vessel even when it is confirmed that the beveled portion 1a of the inner needle 1 is present in the blood vessel by means of flushback after the catheter insertion device is thrust into the blood vessel, resulting in low reliability in securing a passage communicating with a blood vessel. FIG. 4 is a graph showing the change in the penetration resistance of the catheter insertion device. A peak b is obtained at a point of time the incision is formed in the blood vessel by the beveled point of the inner needle, a peak c is obtained at a moment the dilator enters into the incision, and a peak d is obtained at a moment the outer catheter enters into the incision. The patient feels pain at peaks and particularly suffers a large pain at each of the peaks b, c and d. When the diameter of the inner needle is not more than 40% of the outside diameter of the outer catheter, the enlargement of the incision in the blood vessel becomes great, so that a large pain is inflicted on the patient.

SUMMARY OF THE INVENTION

It is, therefore, an object of the present invention to provide an improved catheter insertion device capable of forming a smaller incision in the blood vessel than the outside diameter of the inner needle without the need for any dilator, so that the production cost can be reduced and the pain inflicted on the patient can be made smaller than that in the case of using the catheter insertion device with the dilator. Another object is to provide an insertion device wherein the distance between the beveled point of the inner needle and the outer-catheter end can be made shorter than that of the catheter insertion device with the dilator, in order to improve the reliability in securing a passage communicating with a blood vessel, as well as to eliminate the above-mentioned problems of the prior art.

According to the present invention, there is provided a catheter insertion device comprising an inner needle having a beveled surface at its distal end; an inner needle hub attached to the proximal end of the inner needle; an outer catheter having a through hole for receiving the inner needle, adapted to receive the inner needle in such a way that its beveled point is slightly projected when the inner needle is inserted from its beveled surface side, and further having a catheter tapered tip portion having a tapering outside diameter at its end; and a catheter hub attached to the proximal end of the outer catheter and adapted to detachably engage with the inner needle hub, wherein the above-mentioned inner needle has an inner needle tapered portion formed in the vicinity of the above-mentioned beveled surface.

In other words, the present invention contrives a substantial integration of the dilator and the inner needle by forming the end of the inner needle into a taper and forming a beveled surface in the vicinity of the tapered portion.

According to preferred embodiments of the present invention, it is suitable that the width of the beveled surface is not more than 90% of the outside diameter of the inner needle, and moreover it is preferable that the beveled surface width is not less than 40% of the outside diameter of the outer catheter. Further, it is preferable that the tapering angle of the tapered portion of the inner needle be from 4 to 16 degrees, particularly from 8 to 10 degrees.

The present invention includes a preferred embodiment wherein the above-mentioned inner needle tapered portion is formed into a truncated cone and another preferred embodiment wherein the tapered portion is formed into an odd-shaped cylinder one substantial half of whose cross section is flattened, the flatness being increased toward the beveled point, while the other substantial half of whose cross section is semicircular. Moreover, the present invention includes still another preferred embodiment wherein the beveled surface is formed by obliquely cutting the inner needle tapered portion; a further preferred embodiment wherein the inner needle is formed having a smaller-diameter tubular portion slightly extending from the inner needle tapered portion toward the beveled point, and the beveled surface is formed by obliquely cutting the inner needle tapered portion and the smaller-diameter tubular portion simultaneously; and a still further preferred embodiment wherein the inner needle is formed having a smaller-diameter tubular portion slightly extending from the inner needle tapered portion toward the beveled point, and the beveled surface is formed by obliquely cutting the smaller-diameter tubular portion.

DESCRIPTION OF THE PREFERRED EMBODIMENTS

Figure 6:
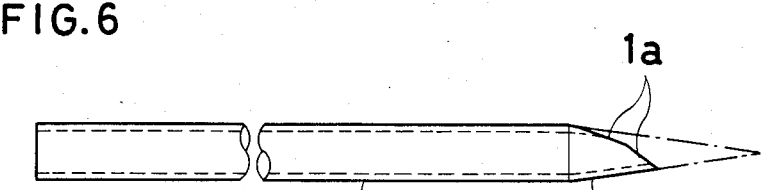
FIGS. 6 and 7 are a side view and a plan view of an inner needle of the catheter insertion device according to the present invention, respectively.
Figure 7:
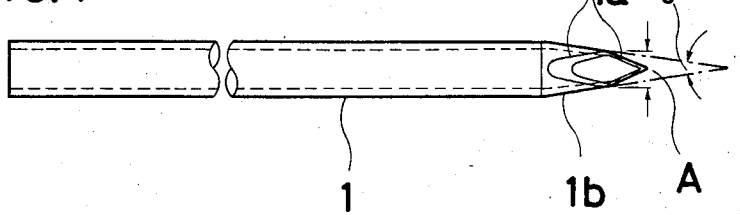

The constitution of a catheter insertion device according to a preferred embodiment of the present invention will be described hereinunder with reference to FIG. 5 thru FIG. 8. The catheter insertion device comprises an inner needle 1 having a beveled surface 1a at its distal end; an inner needle hub 6 attached to the proximal end of the inner needle 1; an outer catheter 2 having a through hole for receiving the inner needle 1, adapted to receive the inner needle 1 in such a way that its beveled point is slightly projected when the inner needle 1 is inserted from the beveled surface side, and further having a catheter tapered tip portion 2a with a tapering outside diameter at its end; and a catheter hub 7 attached to the proximal end of the outer catheter 2, having a flange 7a and adapted to detachably engage with the inner needle hub 6. The inner needle 1 and the outer catheter 2 are made of either metal or plastics, and the same is the case with the inner needle hub 6 and the catheter hub 7. The above-mentioned constitution is not particularly different from a conventional catheter insertion device. New constituent parts will be described hereinunder. As shown in FIG. 6 and FIG. 7, an inner needle tapered portion 1b of a truncated cone shape having a tapering angle $\theta$ of from 4 to 16 degrees is formed in the vicinity of the above-mentioned beveled surface 1a at the end of the inner needle 1. The beveled surface 1a is formed by cutting the inner needle tapered portion 1b obliquely at a given angle so that the width of the beveled surface 1a is not more than 90% of the inner needle outside diameter (e.g., 1 mm$\phi$), preferably not more than 80% (0.8 mm$\phi$).

The basis of numerically limiting the width of the beveled surface 1a so as to be not more than 90%, preferably not more than 80%, of the inner needle outside diameter is according to the following experimental data.

Table 1 was obtained by puncturing a butyl rubber sheet (thickness: 0.7 mm; assumed to be a blood vessel wall) with a catheter insertion device (inner needle outside diameter: 1 mm$\phi$, outer catheter outside diameter: 1.4 mm$\phi$), at five positions and measuring the time needed for 10 cc of water to leak out when a water pressure of 100 cm $H_2O$ is applied.

TABLE 1

| beveled surface width (%) | 100 | 95 | 90 | 85 | 80 | 75 | 70 |

TABLE 1-continued

| (proportion to inner needle outside diameter) | | | | | | | |
|---|---|---|---|---|---|---|---|
| time (minute) | 2 | 3 | 5 | 9 | 13 | 18 | 25 |

Figure 8:
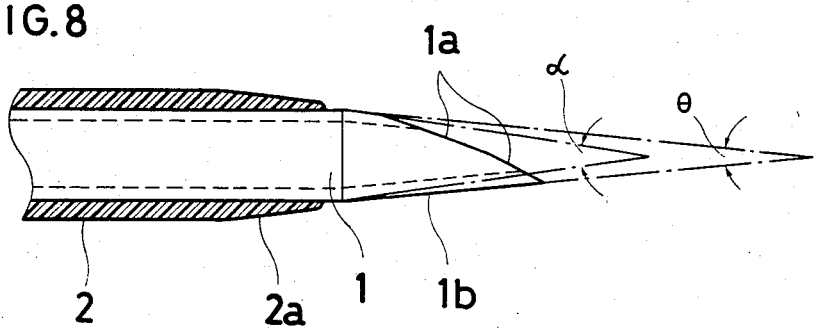
FIG. 8 is an enlarged view of the catheter insertion device shown in FIG. 5.

On the other hand, when a metal pipe is employed as the outer catheter, as shown in FIG. 8, it is proper that the tapering angle α of the tapered tip portion 2a thereof should be from 4 to 16 degrees in accordance with the tapering angle θ of the inner needle tapered portion 1b, while when a plastic pipe is employed, it is preferable to make the angle larger. The above-mentioned inner needle tapered portion 1b is formed by drawing the inner needle end by means of swaging or the like in order to make the beveled surface smaller than the inner needle outside diameter. The tapering angle, from 4 to 16 degrees, is calculated as a range within which the length from the beveled point to the rear end of the inner needle tapered portion can be held not more than 4.5 mm when the width of the beveled surface 1a is set so as to be not more than 90%, preferably not more than 80%, of the inner needle outside diameter as mentioned above. Because as the degree of the enlargement of the incision formed in the blood vessel increases, the pain inflicted on the patient becomes larger, it is necessary to set the width A of the beveled surface 1a of the inner needle 1 so as to be not less than 40%, preferably not less than 50%, of the outside diameter of the outer catheter 2 in order to alleviate the pain. Accordingly, it is desirable that the width of the beveled surface 1a is not more than 90%, preferably not more than 80%, of the inner needle outside diameter so that a hemostatic effect is shown, as well as not less than 40%, preferably not less than 50%, of the outside diameter of the outer catheter 2 in order to minimize the pain inflicted on the patient.

Accordingly, the thinner the wall thickness of the outer catheter 2 becomes, the smaller the width of the beveled surface 1a can be made. However, when using plastics, the wall thickness of the outer catheter 2 has to be not less than 0.2 mm in view of strength requirement. Therefore, if the inner needle outside diameter is 1 mm, the outer catheter outside diameter is 1.4 mm, so that the width of the beveled surface 1a can be determined within an extremely small range: from 0.8 to 0.7 mm. Thus, it is desirable that the tapering angle θ is from 4 to 16 degrees, preferably from 8 to 10 degrees, according to the present invention from the necessity of holding the width of the beveled surface 1a within from 0.8 to 0.7 mm as well as the length from the beveled point to the rear end of the inner needle tapered portion under 4.5 mm.

In addition, the beveled surface 1a is formed into a two-staged taper as shown in FIG. 6 and FIG. 7. This is, however, not exclusive.

Moreover, the inner needle hub 6 is shown as having an air relief passage 6a for communicating the inner passage at the rear of a liquid-tight air-permeable member 8 adapted to close the inner passage with the outside besides the rear end opening of the inner passage, in order to relieve the air in the inner needle passage flushed back when the rear end opening of the inner passage is closed with a finger in use.

Figure 9:
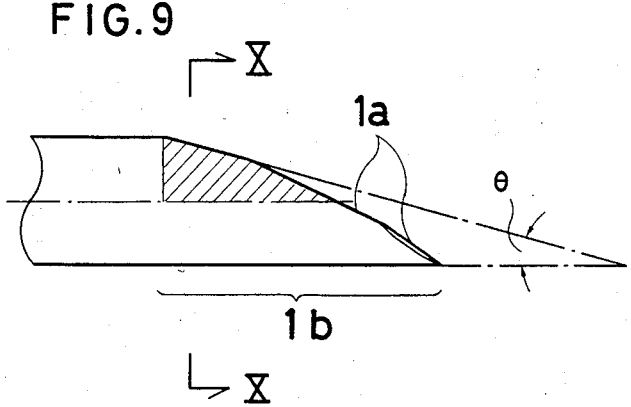
FIG. 9 is a side view of part of the inner needle of the catheter insertion device according to another preferred embodiment of the present invention.
Figure 10:
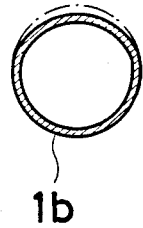
FIG. 10 is a sectional view taken along a line X-X of FIG. 9.

As shown in FIG. 9 and FIG. 10, the present invention includes another preferred embodiment wherein the inner needle is formed into an odd-shaped cylinder having longitudinally cut halves, only one of which is tapered and has a slightly crushed shape, i.e., one substantial half of the cross section of the cylinder is inwardly flattened and the flatness increases toward the beveled point (the hatching portion in FIG. 9) while the other substantial half of the cross section is semicircular, and the beveled surface 1a is formed by cutting the flattened half of the odd-shaped cylinder 1b larger than the half having a semicircular cross section. Further, the tapering angle θ of the flattened half seen in the direction perpendicular to the paper surface is set so as to be from 4 to 16 degrees, preferably from 8 to 10 degrees.

Figure 11:
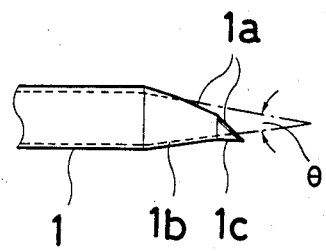
FIGS. 11 and 12 are side views of parts of the inner needles of the catheter insertion device according to still another preferred embodiment, and a further preferred embodiment of the present invention, respectively.
Figure 12:
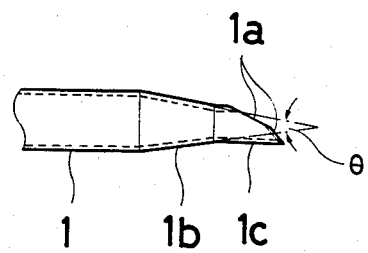

As shown in FIG. 11, the constitution of the present invention may be such that the inner needle has a smaller diameter tubular portion 1c slightly extending from the inner needle tapered portion 1b toward the beveled point and further having a beveled surface 1a formed by obliquely cutting the inner needle tapered portion 1b and the smaller diameter tubular portion 1c simultaneously. As shown in FIG. 12, the constitution of the present invention may be such that the inner needle has a smaller-diameter tubular portion 1c slightly extending from the inner needle tapered portion 1b toward the beveled point and further having a beveled surface 1a formed by obliquely cutting the smaller-diameter tubular portion 1c.

Figure 13:
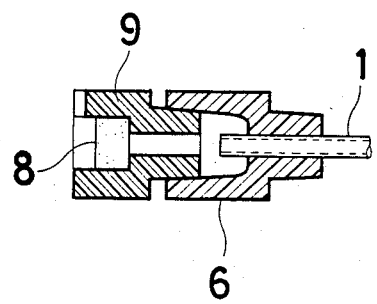
FIG. 13 is a sectional view of the proximal end of a catheter insertion device according to a still further preferred embodiment of the present invention.

As shown in FIG. 13, the constitution of the present invention may be such that a cap 9 having the liquid-tight air-permeable member 8 provided with the air relief passage and adapted to close the passage, is fitted into the inner needle hub 6.

Figure 14:
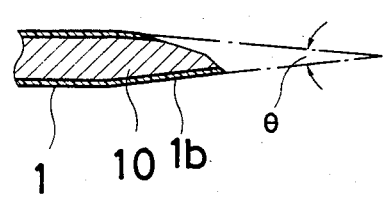
FIG. 14 is a vertical sectional view of the ends of the inner needle and the stylet of a catheter insertion device with the stylet, according to a still further preferred embodiment of the present invention.

As shown in FIG. 14, the constitution of the present invention may be such that a stylet 10 is provided in the passage in the inner needle 1 in order to prevent the blood vessel wall from being cut out by the beveled surface of the inner needle when it punctures the blood vessel wall in case the inner needle has a large outside diameter.

Figure 15:
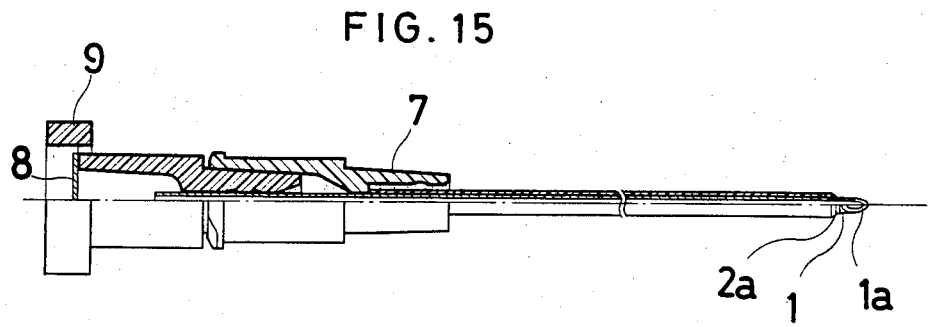
FIG. 15 is a partly sectioned side elevational view of a catheter insertion device with a catheter hub and having no flange, according to a still further preferred embodiment of the present invention.

As shown in FIG. 15, the constitution of the present invention may be such that a catheter hub 7 with no flange is provided at the rear end of the outer catheter.

The catheter insertion device according to the present invention described above is an over-the-needle type catheter insertion device comprising the inner needle, the inner needle hub, the outer catheter and the catheter hub, wherein the inner needle has an inner needle tapered portion formed in the vicinity of the beveled surface.

Figure 1:
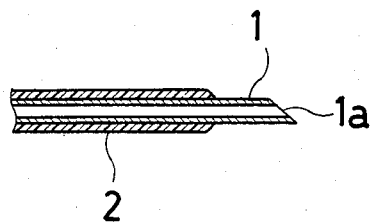
FIG. 1 is a vertical sectional view of an essential part of a conventional catheter insertion device.
Figure 2:
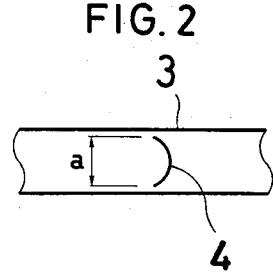
FIG. 2 illustrates an incision in a blood vessel formed by a catheter insertion device.
Figure 3:
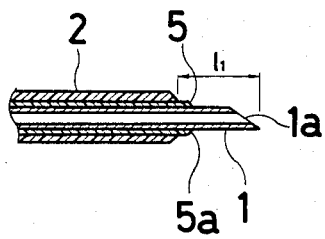
FIG. 3 is a vertical sectional view of an essential part of a conventional catheter insertion device obtained by improving the catheter insertion device shown in FIG. 1.
Figure 4:
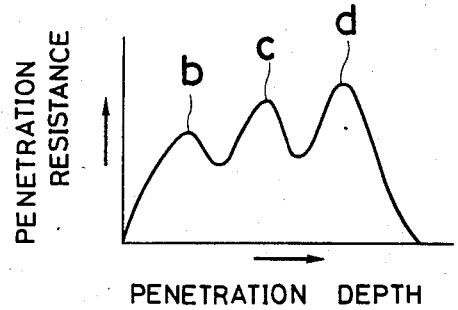
FIG. 4 is a graph showing the penetration resistance of the catheter insertion device shown in FIG. 3.
Figure 5:
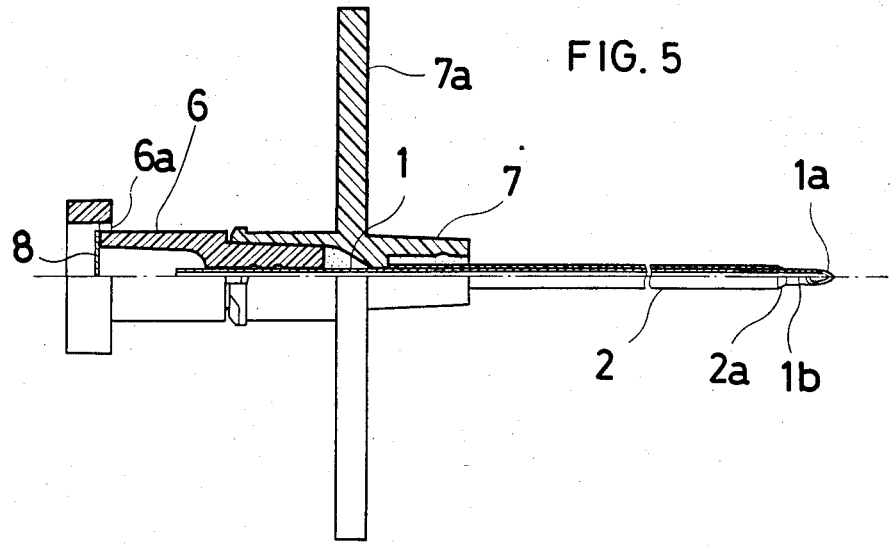
FIG. 5 is a partly sectioned side elevational view of a catheter insertion device according to the present invention.
Figure 16:
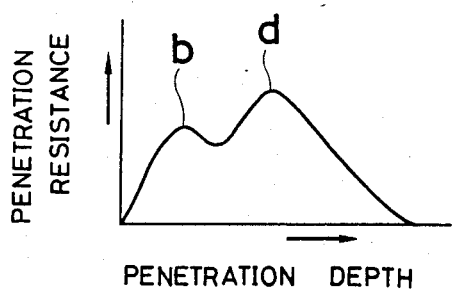
FIG. 16 is a graph showing the penetration resistance of the catheter insertion device according to the present invention shown in FIG. 5 thru FIG. 8.

Accordingly, it is easy to conduct hemostasis because the width of the incision formed in the blood vessel is smaller than the outside diameter of the inner needle and equal to the width of the beveled surface. In addition, because the catheter insertion device according to the present invention has the tapered portion, for enlarging the incision, integrally formed with the inner needle, there are only two peaks, b and d, in the penetration resistance as shown in FIG. 16, and the value of the peak b is almost equal to the peak b shown in FIG. 4. Therefore, it is possible to minimize the pain inflicted on the patient, and the catheter insertion device readily punctures the blood vessel. Further, there is no possiblity of such a failure in securing a passage communicating with a blood vessel as frequently invited by the catheter insertion device shown in FIG. 3, because according to the present invention the length from the beveled point of the inner needle to the outer catheter can be made shorter than that of the catheter insertion device shown in FIG. 3 owing to the elimination of the dilator. Moreover, it is possible to make the production cost lower than that of the catheter insertion device shown in FIG. 3 although the inner needle tapered portion is formed at the end of the inner needle by means of swaging or the like, because the catheter insertion device according to the present invention has no dilator. Furthermore, as a form covering the present invention, when the width of the beveled surface is made not more than 90% of the outside diameter of the inner needle, the incision formed in the blood vessel is smaller than the inner needle outside diameter, so that the blood vessel wall clamps the inner needle. Therefore, less blood leaks out from the blood vessel incision when a guide wire is inserted therein in the case where the catheter insertion device is used as a needle for introducing an angiography catheter.

As another form covering the present invention, when the width of the beveled surface is not less than 40% of the outside diamter of the catheter, the enlargement of the incision formed in the blood vessel can be held within limits of a given proportion, so that the pain inflicted on the patient is prevented from becoming larger.

As still another form covering the present invention, when the tapering angle of the inner needle tapered portion is set so as to be from 4 to 16 degrees, particularly from 8 to 10 degrees, it is easy to form a beveled surface effective in hemostasis while it is possible to obtain dimensions for a beveled point by which a blood vessel passage is readily secured in puncture.

It is to be noted also that the present invention is carried out in a variety of forms. One such form is that the inner needle tapered portion is formed into a truncated cone, and the present invention includes such a form that the inner needle tapered portion is formed into an odd-shaped cylinder such as by slightly flattening one side of a truncated cone. Moreover, the present invention does not exclude such a form that a smaller-diameter tubular portion is provided on the converging side of the inner needle tapered portion, and the beveled surface is provided extending over the inner needle tapered portion and the smaller-diameter tubular portion or only at the smaller-diameter tubular portion.

What I claim is:

1. In a catheter insertion device comprising an inner needle having a beveled surface at its distal end which forms a beveled point at said distal end; an inner needle hub attached to the proximal end of said inner needle; an outer catheter having an axially extending bore means for receiving said inner needle and adapted to receive said inner needle in said bore means so that said beveled point formed by said beveled surface is slightly projected from said outer catheter when said inner needle is inserted, and further having a catheter portion with a tapering outside diameter at its distal end; and a catheter hub attached to the proximal end of said outer catheter and adapted to detachably engage with said inner needle hub, the improvement comprising
said inner needle has an inner needle tapered portion at the distal portion thereof, said beveled surface being partially formed in said inner needle tapered portion and forming said beveled point at said distal end of said needle, said inner needle tapered portion being longer than said beveled surface portion in the axial direction of said inner needle, wherein the width of said beveled surface is not more than 90% of the outside diameter of said inner needle and not less than 40% of the outside diameter of said outer catheter, the tapering angle of said inner needle tapered portion is from 4 to 16 degrees, and the length from the beveled point to the rear end of the inner needle tapered portion is not more than 4.5 mm.

2. A catheter insertion device as defined in claim 1, wherein the width of said beveled surface is not more than 80% of the outside diameter of said inner needle.

3. A catheter insertion device as defined in claim 1 or 2, wherein the width of said beveled surface is not less than 50% of the outside diameter of said outer catheter.

4. A catheter insertion device as defined in claim 1, wherein the tapering angle of said inner needle tapered portion is from 8 to 10 degrees.

5. A catheter insertion device as defined in claim 1, wherein said inner needle tapered portion is in the form of truncated cone.

6. A catheter insertion device as defined in claim 1, wherein said inner needle tapered portion is in the form of an odd-shaped cylinder one substantial half of whose cross section is inwardly flattened so that the flatness becomes gradually larger toward the beveled point and the other substantial half of whose cross section is semicircular.

7. A catheter insertion device as defined in claim 1, wherein said beveled surface is in the form of an oblique cut through said inner needle tapered portion.

8. In a catheter insertion device comprising an inner needle having a beveled surface at its distal end which forms a beveled point at said distal end; an inner needle hub attached to the proximal end of said inner needle; an outer catheter having an axially extending bore means removably receiving said inner needle and adapted to receive said inner needle in said bore means so that said beveled point formed by said beveled surface is slightly projected from said outer catheter when said inner needle is inserted, and further having a catheter tapered portion with a tapering outside diameter at its distal end; and a catheter hub attached to the proximal end of said outer catheter and adapted to detachably engage with said inner needle hub, the improvement comprising:
said inner needle has an inner needle tapered portion formed in the vicinity of said beveled surface, wherein the width of said beveled surface is not more than 90% of the outside diameter of said inner needle and not less than 40% of the outside diameter of said outer catheter, the tapering angle of said inner needle tapered portion is from 4 to 16 degrees, and the length from the beveled point to the rear end of the inner needle tapered portion is not more than 4.5 mm;
said inner needle having a smaller-diameter tubular portion slightly extending from said inner needle tapered portion toward the beveled point; and
said beveled surface is in the form of an oblique cut through both said inner needle tapered portion and said smaller-diameter tubular portion.

9. In a catheter insertion device comprising an inner needle having a beveled surface at its distal end which forms a beveled point at said distal end; an inner needle hub attached to the proximal end of said inner needle; an outer catheter having an axially extending bore means removably receiving said inner needle and adapted to receive said inner needle in said bore means so that said beveled point formed by said beveled surface is slightly projected from said outer catheter when said inner needle is inserted, and further having a catheter tapered portion with a tapering outside diameter at its distal end; and a catheter hub attached to the proximal end of said outer catheter and adapted to detachably engage with said inner needle hub, the improvement comprising:

said inner needle has an inner needle tapered portion formed in the vicinity of said beveled surface, wherein the width of said beveled surface is not more than 90% of the outside diameter of said inner needle and not less than 40% of the outside diameter of said outer catheter, the tapering angle of said inner needle tapered portion is from 4 to 16 degrees, and the length from the beveled point to the rear end of the inner needle tapered portion is not more than 4.5 mm;

said inner needle having a smaller-diameter tubular portion slightly extending from said inner needle tapered portion toward the beveled point; and said beveled surface is in the form of an oblique cut through said smaller-diameter tubular portion.

* * * * *

UNITED STATES PATENT AND TRADEMARK OFFICE
CERTIFICATE OF CORRECTION

PATENT NO.   :   4,565,545
DATED        :   January 21, 1986
INVENTOR(S)  :   T. SUZUKI It is certified that error appears in the above-identified patent and that said Letters Patent is hereby corrected as shown below:

COLUMN 5, line 41, change "requirement" to

--requirements--.

Signed and Sealed this

Seventh Day of October, 1986

[SEAL]

Attest:

DONALD J. QUIGG

Attesting Officer

Commissioner of Patents and Trademarks